United States Patent
Wernicki

(10) Patent No.: US 8,018,588 B2
(45) Date of Patent: Sep. 13, 2011

(54) SAMPLE HOLDER AND SAMPLE PREPARATION DEVICE

(75) Inventor: Alice Wernicki, West Lafayette, IN (US)

(73) Assignee: Aptuit, Inc., Greenwich, CT (US)

(*) Notice: Subject to any disclaimer, the term of this patent is extended or adjusted under 35 U.S.C. 154(b) by 210 days.

(21) Appl. No.: 12/133,675

(22) Filed: Jun. 5, 2008

(65) Prior Publication Data

US 2008/0316465 A1 Dec. 25, 2008

Related U.S. Application Data

(60) Provisional application No. 60/942,448, filed on Jun. 6, 2007.

(51) Int. Cl.
*G01N 21/01* (2006.01)

(52) U.S. Cl. .................................................. 356/244

(58) Field of Classification Search .......... 356/244; 73/64.56, 863, 863.31, 863.33, 864.91; 378/208
See application file for complete search history.

(56) References Cited

U.S. PATENT DOCUMENTS

| | | | |
|---|---|---|---|
| 4,060,646 A | 11/1977 | Bringi et al. | |
| 4,290,835 A | 9/1981 | Yates et al. | |
| 4,295,857 A | 10/1981 | Schuler et al. | |
| 4,641,329 A | 2/1987 | Green et al. | |
| 5,009,861 A | 4/1991 | Plaas-Link | |
| 5,200,910 A | 4/1993 | Subbiah | |
| 5,221,410 A | 6/1993 | Kushner et al. | |
| 5,363,797 A | 11/1994 | Uenishi et al. | |
| 5,614,726 A | 3/1997 | Kaye et al. | |
| 5,997,636 A | 12/1999 | Gamarnik et al. | |
| 5,998,018 A * | 12/1999 | Murakami et al. | 428/343 |
| 6,150,380 A | 11/2000 | Lovqvist et al. | |
| 6,267,935 B1 | 7/2001 | Hol et al. | |
| 6,371,640 B1 | 4/2002 | Hajduk et al. | |
| 6,507,636 B1 | 1/2003 | Lehmann | |
| 6,642,060 B2 | 11/2003 | Morris et al. | |

(Continued)

FOREIGN PATENT DOCUMENTS

JP 06095190 A 4/1994

(Continued)

OTHER PUBLICATIONS

Final Office Action dated Jul. 19, 2010 in U.S. Appl. No. 12/133,639.

(Continued)

*Primary Examiner* — Roy Punnoose
(74) *Attorney, Agent, or Firm* — J.A. Lindeman & Co., PLLC

(57) ABSTRACT

An apparatus for forming a solid sample from a sample solution and then analyzing the solid sample to determine the solid form of the sample is provided. The apparatus may optionally comprise a masking block with an array of openings, a film on which the solid sample can be deposited, and a sheet. The apparatus may optionally comprise a masking block with an array of openings and a sheet on which the sample can be deposited. The apparatus may comprise the formation unit of a system for forming a solid sample and analyzing the solid sample. The system may further comprise an analysis unit comprising the film and/or sheet with the solid samples and a spacer unit attached to the film after it has been removed from the formation unit. Methods for using the apparatus and/or system of the present invention are also provided.

25 Claims, 3 Drawing Sheets

U.S. PATENT DOCUMENTS

| | | | |
|---|---|---|---|
| 6,750,064 | B2 | 6/2004 | Stahly et al. |
| 6,836,532 | B2 | 12/2004 | Durst et al. |
| 6,937,330 | B2 * | 8/2005 | Dietz et al. .................... 356/246 |
| 7,041,169 | B2 | 5/2006 | Morris et al. |
| 7,269,245 | B2 | 9/2007 | He et al. |
| 2002/0048610 | A1 | 4/2002 | Cima et al. |
| 2002/0179835 | A1 | 12/2002 | Feygin |
| 2004/0234421 | A1 | 11/2004 | Moll et al. |
| 2004/0251414 | A1 * | 12/2004 | Rodewald ................ 250/339.07 |

FOREIGN PATENT DOCUMENTS

| | | |
|---|---|---|
| WO | WO 00/67872 | 11/2000 |
| WO | WO 02/052919 | 7/2002 |

OTHER PUBLICATIONS

Abstract of JP 06095190 A, Apr. 8,1994.

Chyall et al., "Polymorph Generation in Capillary Spaces: The Preparation and Structural Analysis of a Metastable Polymorph of Nabumetone," *Crystal Growth and Design*, 2(6):505-510 (2002).

Kajola, "Syntheses in capillary tubes," *Acta Chem. Scand.*, 8:698-9 (1954).

Stephenson et al., "Solid-State Analysis of Polymorphic, Isomorphic, and Solvated Forms of Dirithromycin," *J. Am. Chem. Soc.*, 116:5766-5773 (1994).

Byrn et al., "Solid-State Chemistry of Drugs,"*SSCI, Inc.* (Second Edition 1999).

Giordano et al., "Crystal Forms of Piroxicam Pivalate: Preparation and Characterization of Two Polymorphs," *J. Pharm. Sci.*, 87(3):333-346 (1998).

Bartolomei et al., "Solid-state investigation of fluocinolone acetonide," *J. Pharm. and Biomedical Analysis*, 15:1813-1820 (1997).

Kiss et al., "Solid state investigation of mefloquine hydrochloride," *J. Pharm. & Biomedical Analysis*, 12(7):889-893 (1994).

Caira et al., "Structure and Thermal Stability of Alprazolam and Selected Solvates," *J. Pharm. Sci.*, 84(11):1379-1384 (1995).

Wu et al., "Investigation of Moricizine Hydrochloride Polymorphs," *J. Pharm. Sci.*, 83(10):1404-1406 (1994).

Hildebrand et al., "Ketoprofen Sodium: Preparation and Its Formation of Mixed Crystals with Ketoprofen," *J. Pharm. Sci.*, 86(7):854-857 (1997).

Agafonov et al., "Polymorphism of Spironolactone," *J. Pharm. Sci.*, 80(2):181-185 (1991).

Chang et al., "Solid State Characterization of Dehydroepiandrosterone," *J. Pharm. Sci.*, 84(10):1169-1179 (1995).

Tros de Ilarduya et al., "Polymorphism of Sulindac: Isolation and Characterization of a New Polymorph and Three New Solvates," *J. Pharm. Sci.*, 86(2):248-251 (1997).

Beckmann, "Seeding the Desired Polymorph: Background, Possibilities, Limitations, and Case Studies," *Organic Process Res. & Dev.*, 4372-383 (2000).

Threlfall, "Crystallization of Polymorphs: Thermodynamic Insight into the Role of Solvent," *Organic Process Res, & Dev.*, 4:384-390 (2000).

Vrcelj et al., "Polymorphism in 2,4,6-Trinitrotoluene Crystallized from Solution," *J. Am. Chem. Soc.*, 123:2291-2295 (2001).

Caira et al., "Structural Characterization of Two Polymorphic Forms of Piroxicam Pivalate," *J. Pharm. Sci.*, 87(12):1608-1614 (1998).

Gu et al., "Characterization of Polymorphic Forms of Fluconazole Using Fourier Transform Raman Spectroscopy," *J. Pharm. Sci.*, 84(12):1438-1441 (1995).

Salem et al., "Preparation, characterization and transformation of terfenadine polymorphic forms," *Int. J. Pharmaceutics*, 141:257-259 (1996).

Hassan, et al., "Characterization of famotidine polymorphic forms," *Int. J. Pharmaceutics*, 149:227-232 (1997).

Ghodbane et al., "Study of the polymorphism of 3-(((3-(2-(7-chloro-2-quinolinyl)-(E)-ethenyl)phertyl) ((3-(3-(dimethylamino-3-oxopropyl)thio)methyl)-thio)propanoic acid (MK571) by DSC, TG, XRPD and Solubility Measurements," *Int. J. Pharmaceutics*, 59:281-286 (1990).

Pienaar et al., "Polymorphs of nitrofurantoin. 2. Preparation and X-ray crystal structures of two anhydrous forms of nitrofurantoin," *J. Crystallographic and Spectroscopic Res.*, 23(10):785-790 (1993).

Chao et al., "Polymorphism of 1,2-Dihydro-6-neopentyl-2-oxonieolinic Acid: Characterization, Interconversion, and Quantitation," *Pharm. Res.*, 4(5):429-432 (1987).

Gavezzotti et al., "Polymorphic Forms of Organic Crystals at Room Conditions: Thermodynamic and Structural Implications," *J. Am. Chem. Soc.*, 117:12299-12305 (1995).

Henck, et al., "Polymorphism of Tedisamil Dihydrochloride," *J. Pharm. Sci.*, 89(9):1151-1159 (2000).

Nomura et al., "Thermal Polymorphic Transformation of *p-tert*-Butylcalix[4]arene Derivatives Bearing Amino Acid Substituents," *J. Org. Chem.*, 65(19):5932-5936 (2000).

Gavezzotti, "A Molecular Dynamics Test of the Different Stability of Crystal Polymorphs under Thermal Strain," *J. Am, Chem. Soc.*, 122:10724-10725 (2000).

Dinnebier et al., "Structural Characterization of Three Crystalline Modifications of Telmisartan by Single Crystal and High-Resolution X-ray Powder Diffraction," *J. Pharm. Sci.*, 89(11):1465-1479 (2000).

Henck et al., "Disappearing and Reappearing Polymorphs. The Benzocaine:Picric Acid System," *J. Am, Chem. Soc.*, 123:1834-1841 (2001).

Threlfall, "Analysis of Organic Polymorphs: A Review," *Analyst*, 120:2435-2448 (1995).

Spruijtenburg, "Examples of the Selective Preparation of a Desired Crystal Modification by an Appropriate Choice of Operating Parameters," *Organic Process Res. & Dev.*, 4:403-406 (2000).

Beckmann et al., "Occurrence, Stability, Kinetics of Crystallization and Polymorphic Transition of the A, B and C Modification of Abecarnil: Influence of Supersaturation, Temperature, Solvents and Impurities," *Institution of Chemical Engineers Trans IChemE*, 74(Part A):750-758 (1996).

Yu et al., "Thermochemistry and Conformational Polymorphism of a Hexamorphic Crystal System," *J. Am. Chem. Soc.*, 122(4):585-591 (2000).

Stephenson et al., "Conformational and Color Polymorphism of 5-Methyl-2-[(2-nitrophenyl)amino]-3-thiophenecarbonitrile," *J. Pharm. Sci.*, 84(11):1385-1386 (1995).

Moore et al., "Crystal and molecular structures of two polymorphs of 4-methyl-2-nitroacetanilide (MNA)," *J. Crystallographic and Spectroscopic Res.*, 13(4):279-292 (1983).

Moore et al., "Crystal and molecular structure of an amber polymorph of 4-methyl-2-nitroacetanilide (MNA)," *J. Crystallographic and Spectroscopic Res.*, 14(3):283-291 (1983).

Singh et al., "Solid-State Characterization of Chlordiazepoxide Polymorphs," *J. Pharrn. Sci.*, 87(5):655-662 (1998).

Harris et al., "'Polymorphism' in a novel anti-viral agent: Lamivudine," *J. Chem. Soc., Perkin Trans.*, 2:2653-2659 (1997).

Caira et al., "Crystal and molecular structures of three modifications of the androgen dehydroepiandrosterone (DHEA)," *J. Chem. Crystallography*, 25(7):393-400 (1995).

Cox et al., "Structure of 3β-Hydroxy-5-androsten-17-one (DHEA) Monohydrate," *Int. Union of Crystallography*, C46:334-336 (1990).

Swanson et al., "Model of the Evaporating Meniscus in a Capillary Tube," *Transactions of the ASME, J. Heat Transfer*, 114:434-441 (1992).

Stewart et al., "The Formation of Particle Clusters Near An Interfacial Meniscus." *Chem. Eng. Sci.*, 48(4):771-788 (1993).

Laurindo et al., "Evaporation in Capillary Porous Media. An Experimental and Numerical Network Study," *Proceedings of the ASME Heat Transfer and Fluids Engineering Divisions*, HTD-321, FED-233:637-649 (1995).

Khrustaiev et al., "Fluid Flow Effects in Evaporation From Liquid-Vapor Meniscus," *Transactions of the ASAIE, J. Heat Transfer*, 118:725-730 (1996).

Kuz, "Model for the Convective Transport of Particles in a Two-Dimensional Cluster," *Am. Chem. Soc.*, Langmuir, 13:3900-3901 (1997).

Frink et al., "Wetting of a chemically heterogeneous surface," *J. Chem, Phy.*, 110(12):5969-5977 (1999).

Amaro-Gonzalez et al., "Gas antisolvent crystallization of organic salts from aqueous solutions," *J. Supercritical Fluids*, 17:249-258 (2000).

Mullin, "Crystallization techniques and equipment," *Crystallization*, Butterworth-Heinemann, pp. 265-368 (1993).

Guillory, "Generation of Polymorphs, Hydrates, Solvates, and Amorphous Solids," *Polymorphism in Pharmaceutical Solids*, pp. 183-226 (Marcel-Dekker, Inc. 1999).

He et al., "Conformational Color Polymorphism and Control of Crystallization of 5-Methyl-2-[(4-methyl-2-nitrophenyl)amino]-3-thiophenecarbonitrile," *J. Pharm. Sci.*, 90(3):371-388 (2001).

Cristian et al., "*The Mechanism of Material Drying* v. *Liquid Evaporation From Capilaries*," *Buletinul Institutului Politehnic Din Iasi, Sectia II*, pp. 37-43 (1979).

Overman et al., "Convective Diffusion in Capillaries," *J. Phy. Chem.*, 72(1):155-158 (1968).

Preiss, et al., "Evaporation From A Capillary Tube," *Transactions of the ASME, Journal of Heat Transfer*, pp. 178-181 (1976).

Christenson, et al., "Growth of Ionic Crystallites on Exposed Surfaces," *J. Colloid and interface Science*, 117(2):576-577 (1987).

Sibille et al., "Analysis of solvent evaporation rates in the vapor diffusion protein crystal growth experiments from STS-61C Space Shuttle Mission," *J. Crystal Growth*, 110:72-79 (1991).

Sibille et al., "Solvent evaporation rates in the enclosed capillary vapor diffusion method of protein crystal growth," *J. Crystal Growth*, 110:80-88 (1991).

Non-Final Office Action dated Dec. 4, 2002 in U.S. Appl. No. 09/752,857 (now U.S. Pat. No. 6,750,064).

Non-Final Office Action dated Jul. 1, 2002 in U.S. Appl. No. 09/752,857 (now U.S. Pat. No. 6,750,064).

Co-pending U.S. Appl. No. 10/842,547.

Advisory Action dated Apr. 2, 2008 in U.S. Appl. No. 10/842,547.

Notice of Panel Decision from Pre-Appeal Brief Review dated Mar. 26, 2008, in U.S. Appl. No. 10/842,547.

Final Office Action dated Sep. 24, 2007 in U.S. Appl. No. 10/842,547.

Non-Final Office Action dated Mar. 26, 2007 in U.S. Appl. No. 10/842,547.

Final Office Action dated Aug. 8, 2006 in U.S. Appl. No. 10/842,547.

Non-Final Office Action dated Dec. 23, 2005 in U.S. Appl. No. 10/842,547.

Non-Final Office Action dated Aug. 18, 2005 in U.S. Appl. No. 10/842,547.

Taylor et al., "Evaluation of Solid-State Forms Present in Tablets by Raman Spectroscopy," *J. Pharm. Sci.*, 89(10):1342-1353 (2000).

Zerkowski et al., "Polymorphic Packing Arrangements in a Class of Engineered Organic Crystals," *Chemistry of Materials*, 9(9):1933-1941, Abstract (1997).

Klein et al., "Combinatorial Material Libraries on the Microgram Scale with an Example of Hydrothermal Synthesis," *Angew. Chem, Int, Ed.*, 37(24):3369-3372 (1998).

Morissette et al., "High-throughput crystallization: polymorphs, salts, co-crystals and solvates of pharmaceutical solids," *Adv. Drug Delivery Rev.*, 56:275-300 (2004).

International Search Report for WO 02/052919 (continuation of U.S. Pat. No. 6,750,064).

International Preliminary Examination Report for WO 02/052919 (continuation of U.S. Pat. No. 6,750,064) dated Apr. 4, 2003.

Moreno et al., "Investigations on gravity influence upon protein crystallization by the gel acupuncture technique," J. *Crystal Growth*, 196(2-4):587-594 (1999).

Moreno et al., "Growth of shaped single crystals of proteins," *J. Crystal Growth*, 166(1):919-924 (1996).

Pitts et al.; "Crystallization by centrifugation," *Nature*, vol. 356:392 (1992).

Shekunov et al., "Crystallization processes in pharmaceutical technology and drug delivery design," *J. Crystal Growth*, 211(1-4):122-136 (2000).

Co-pending U.S. Appl. No. 12/133,639.

Non-Final Office Action dated Jun. 26, 2009 in U.S. Appl. No. 12/133,639.

Final Office Action dated Mar. 1, 2010 in U.S. Appl. No. 12/133,639.

Apparel Search, Polypropylene Definition to Educate the Apparel Industry, Apr. 10, 2007, http://www.apparelsearch.com/Definitions/Fiber/Polypropylene_definition.htm.

PolyFab, Industry Glossary: Polypropylene, 2003, http://www.polyfab.org/corporate/glossary.htm.

\* cited by examiner

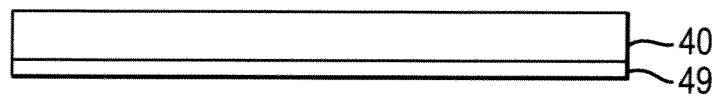
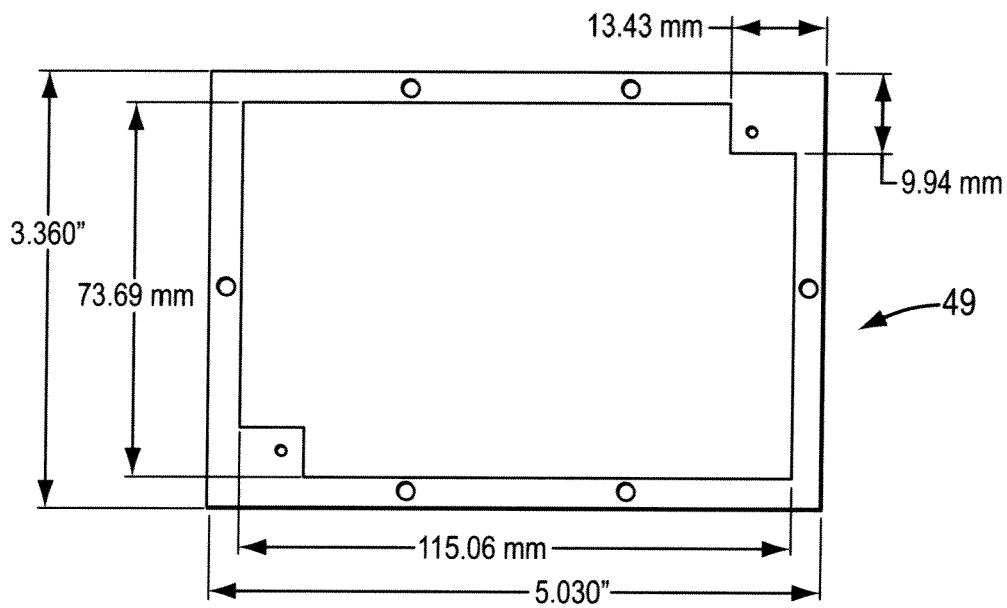
Figure 4a
Figure 4b
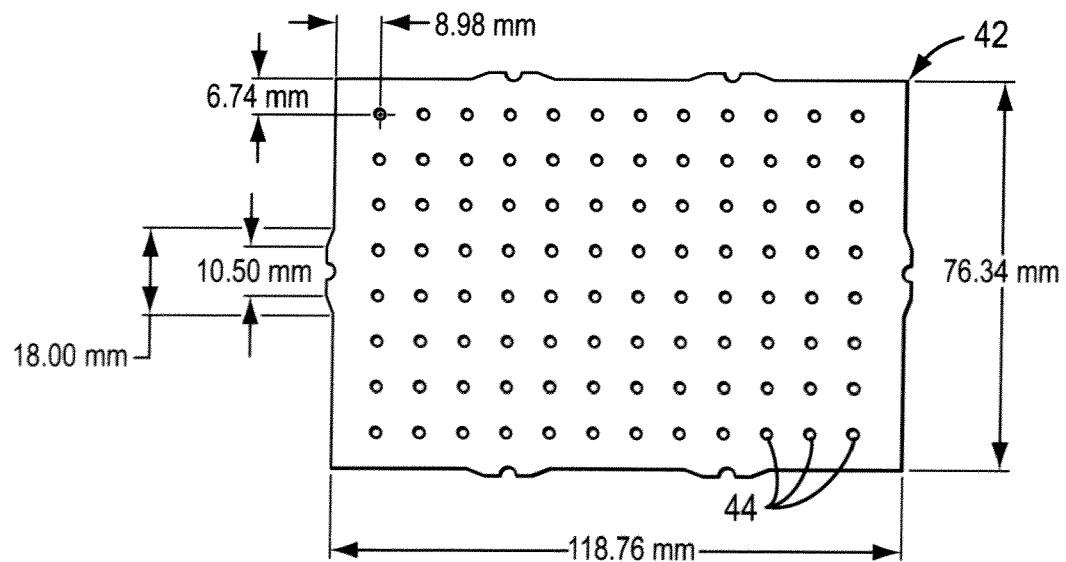
Figure 4c

SAMPLE HOLDER AND SAMPLE PREPARATION DEVICE

This application claims priority to U.S. Provisional Patent Application No. 60/942,448, filed Jun. 6, 2007.

BACKGROUND

The present invention generally relates to devices used as sample holders and sample preparation devices for characterization of solid-state chemical compounds formed in the devices and more particularly to such devices used for rapid screening of solid form libraries.

As is well known, many organic and inorganic compounds can exist in the solid phase in different states, for example, crystalline, quasi-crystalline, nanocrystalline, and/or amorphous solids. These different solid phases may also exhibit different solid forms. The existence of different solid forms of a compound is important because the physical form of a solid can affect its properties, such as, for example, solubility, water sorption and desorption properties, particle size, hardness, drying characteristics, flow and filterability, compressibility, and density. Different solid forms can have different melting points, spectral properties, and thermodynamic stability. In the field of pharmaceuticals, for example, understanding whether a new chemical entity exists in different solid forms is important. Examples of solid forms of a compound would include different salt forms, cocrystals, polymorphs, solvates, and/or hydrates. Determining the solid form of a compound can include analyzing a solid to ascertain the form of the solid. For example, it may be determined that a solid is crystalline. In another instance, one might determine that the solid form is a multicomponent crystal, otherwise known as a cocrystal, such as a hydrate or solvate. As a further example, if the same chemical compound solidifies into different crystal structures, then that compound is deemed to be polymorphic.

Determining the solid form of a compound is particularly important in the pre-formulation stage of development because in a drug substance, variations in properties associated with different forms can lead to differences in dissolution rate, oral absorption, bioavailability, levels of gastric irritation, toxicology results, and clinical trial results, for example. Ultimately both safety and efficacy are impacted by properties that vary among different solid forms. Accordingly, the importance of screening a compound for solid forms ("screening") is commonly understood.

Screening may be a function of time and effort, with the quality or results of screening being a function of the number of samples prepared and/or analyzed as well as the quality of preparation and/or analysis underlying those samples. Therefore, it is generally desirable to use numerous experimental parameters during a screen of a compound in order to maximize the number of viable solid forms identified and characterized. This generally requires that a very large number of experiments be performed.

One traditional way to screen a compound to determine whether it exists in multiple solid forms is to use individual glass vials for each experiment. Once the experiment is complete, the sample is then transferred to an appropriate holder and labelled before analysis using techniques such as, for example, X-ray powder diffraction (XRPD) in transmission or reflection mode, Raman spectroscopy including Raman microscopy, infrared spectroscopy (IR) including IR microscopy, near IR, or optical microscopy. One disadvantage associated with this method, however, is the amount of time it takes to prepare each sample, i.e., to put the compound of interest, appropriate solvent, and any other desired component of the experiment into individual vials, and then to transfer it to the appropriate holder, label it, and perform the desired analytical technique or techniques. If a large number of experiments is to be performed, the amount of time required to run a screen with this method may be prohibitive. Another disadvantage is that this method requires a relatively large amount of material for each experiment.

Accordingly, it is known to use a "microtiter plate" or a "microplate," which is an apparatus comprising a plurality of wells. Each well of a microplate can typically hold in the range of a few to a few hundred or more microliters of liquid. The microplates, which are often made of polystyrene or polypropylene, can be clear or opaque.

Using a microplate, the compound of interest, appropriate solvent if applicable, and any other desired component of the experiment can be disposed in each of the wells. Such microplates, which typically comprise 6, 24, 96, 384, or even 1536 or more wells arranged in an array, thus allow multiple experiments to be run simultaneously. This procedure thus significantly reduces the amount of time required to perform the desired large number of experiments in a screen.

Once the experiments are completed and the solvent, if used, is removed, the samples in the microplate can be analyzed in situ, thereby eliminating the step of transferring the sample to a holder. This also allows for a smaller amount of materials to be used in each experiment. One disadvantage associated with conventional microplates, however, is that when the sample is analyzed, for example by XRPD or Raman spectroscopy including Raman microscopy, the material that the microplate is composed of can interfere with the analysis, for example at the well bottom or microplate bottom ("bottom portion"). This can, for example, produce unwanted spectral interference in or contribution to the analytical data, such as the Raman spectrum or XRPD pattern, which can significantly affect the quality of the data obtained.

In an alternative conventional way of screening a compound, an apparatus can be used which consists of a glass plate that is attached under pressure to a block of material that has thru holes with o-rings or another type of gasket, creating a liquid tight seal between the glass plate and the block with holes. After solids are produced in the apparatus, the solids are scraped to the bottom of the apparatus, and the block with holes and the o-rings are removed, so that the solids remain on the glass plate. There are several disadvantages to this type of apparatus, however, including for example that the solid material sticks to or lodges under the o-rings. Another disadvantage is that with the removal of the block with holes and o-rings, there are unprotected piles of solid on the glass plate with nothing to prohibit cross-contamination of the piles. Additionally, with smaller samples requiring smaller holes in the block, smaller o-rings and gaskets are required. These usually need to be custom manufactured. Finally, the composition of the o-rings needs to be matched to each of the solvents used to prevent degradation of the o-rings and contamination of the samples.

As can be seen, there is a need for a sample holder apparatus that allows for flexibility in sample size and eliminates or decreases cross-contamination between samples or interference by the sample holder with the analysis of the sample. Although not required, in some embodiments it may also be advantageous if such a sample holder could be disposable.

Although the present invention may obviate one or more of the above-mentioned disadvantages, it should be understood that some aspects of the invention might not necessarily obviate one or more of those disadvantages.

In the following description, various aspects and embodiments will become evident. In its broadest sense, the invention could be practiced without having one or more features of these aspects and embodiments. Further, these aspects and embodiments are exemplary. Additional objects and advantages of the invention will be set forth in part in the description which follows, and in part will be obvious from the description, or may be learned by practicing of the invention. The objects and advantages of the invention will be realized and attained by means of the elements and combinations particularly pointed out in the appended claims.

SUMMARY OF THE INVENTION

In accordance with exemplary embodiments of the invention, there is thus provided an improved apparatus and system for the formation of solids and analysis of solid forms, and improved methods of forming solids and analyzing solid forms.

In one exemplary embodiment of the invention there is provided an apparatus for the formation of solids and analysis of solid forms comprising a masking block with an array of openings and a sheet, wherein the sheet forms a liquid tight seal with the masking block.

In another exemplary embodiment of the invention, there is provided an apparatus for the formation of solids and analysis of solid forms comprising a masking block with an array of openings, a sheet, and a film, wherein the film can be located between the masking block and the sheet, and wherein the film can form a liquid tight seal with the masking block.

In another exemplary embodiment of the invention, there is provided a system for the formation of solids and analysis of solid forms of the solids comprising a formation unit and an analysis unit. The formation unit may comprise a masking block with an array of openings, a sheet, and a film on which the array of solids is deposited, wherein the film can be located between the masking block and the sheet and can be separable from the masking block and sheet, and wherein the film can form a liquid tight seal with the masking block. The sheet can also be separable from the masking block and can also form a liquid tight seal with the masking block. The analysis unit may comprise the film with an array of solids, wherein the film can be separated from the masking block and the sheet; a spacer plate, wherein the spacer plate can have approximately the same array of holes as the masking block; and wherein the film can be attached to the spacer plate.

In another exemplary embodiment of the invention there is provided a system for the formation of solids and analysis of solid forms comprising a formation unit and an analysis unit. The formation unit may comprise a masking block with an array of openings and a sheet on which the array of solids can be deposited, wherein the sheet can be separable from the masking block and wherein the sheet can form a liquid tight seal with the masking block. The analysis unit may comprise the sheet with an array containing the solids to be analyzed, wherein the sheet can be separated from the masking block; a spacer plate, wherein the spacer plate can have approximately the same array of holes as the masking block; and wherein the sheet can be attached to the spacer plate.

In another exemplary embodiment of the invention, there is provided a method of forming a solid and then analyzing the solid form comprising the steps of (a) placing at least one aliquot of a liquid containing one or more solvents and at least one organic or inorganic chemical compound in an opening of a formation unit, the formation unit comprising a masking block comprising an array of openings, a film, and a sheet, wherein the film can be located between the masking block and the sheet, and wherein the film can form a liquid tight seal with the masking block, (b) removing solvent from the sample aliquot, (c) depositing the solid, and (d) analyzing the solid to determine the solid form produced.

In another exemplary embodiment of the invention there is provided a method of forming a solid and analyzing the solid form comprising the steps of (a) placing at least one aliquot of a liquid containing one or more solvents and at least one organic or inorganic chemical compound in an opening of a formation unit, the formation unit comprising a masking block comprising an array of openings, and a sheet, wherein the sheet can form a liquid tight seal with the masking block, (b) removing solvent from the sample aliquot, (c) depositing the solid, and (d) analyzing the solid to determine the solid form produced.

By "liquid tight seal" it is meant that the liquid aliquot placed in any opening of the array of an exemplary masking block will remain on the surface of the material adjacent to the masking block, and will not contaminate samples in other openings on the material adjacent to the masking block.

The film useful according to exemplary embodiments of the present teachings includes films that are either malleable or not malleable. The term "sheet" as used herein is meant to include materials that are either malleable or not malleable. By masking block it is meant to include masking blocks made of materials that are either malleable or not malleable. At least one of the masking block, film, and sheet should have sufficient malleability to allow for the formation of a liquid tight seal.

By the use of singular terms herein, such as for example "sheet" and "film," it is understood that a plurality of the component may also be used. For example, either the sheet or the film herein may comprise either a single sheet or film, or may comprise a plurality of sheets or films, and the use of the singular is not intended to exclude the use of more than one sheet or film according to the present teachings.

By "approximately the same array" it is meant that the spacer plate has a configuration of openings that is similar to those of the masking block, i.e. that the center-to-center distances of the masking block and spacer plate are the same within experimental error.

By "deposited" it is meant that solids may form in locations other than on the films of the invention. For example, a solid may form inside the masking block and it may be necessary to physically transfer the solid to the film for analysis. Such a physical transfer is an example of depositing the solid onto the film.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention. In the drawings:

FIG. 2b is a top plan view of the exemplary sample holder of FIG. 2a;

FIG. 4a is a cross-sectional view of an exemplary holder for an analysis unit, according to various aspects of the present teachings;

FIG. 4b is a top plan view of the exemplary sample holder of FIG. 4a; and

FIG. 4c is a top plan view of an exemplary spacer plate.

DESCRIPTION OF EXEMPLARY EMBODIMENTS

Reference will now be made in greater detail to exemplary embodiments of the invention, examples of which are illustrated in the accompanying drawings.

One exemplary embodiment according to the present teachings provides an apparatus for forming solids and analyzing solid forms comprising a masking block with an array of openings, a film on which the solids are deposited and a sheet. The film may be positioned between the masking block and the sheet, and a liquid tight seal may be formed between the film and the masking block. Alternatively, the apparatus may comprise a masking block and a sheet of where a liquid tight seal may be formed between the sheet and the masking block. The apparatus may further comprise a bottom support plate for supporting the sheet and/or film. The apparatus may also be part of a system wherein the system further comprises a spacer plate. The film may be removed from between the masking block and the sheet and may be attached to the spacer plate. A spacer plate with the film attached may optionally be sealed with a second film.

Another exemplary embodiment according to the present teachings provides methods for forming and analyzing solid forms using an exemplary apparatus according to the present teachings, which may comprise the steps of (a) placing at least one aliquot of a liquid containing one or more solvents and at least one organic or inorganic chemical compound into at least one opening of a masking block with an array of openings, a film on which the solids are deposited and a sheet, (b) removing the liquid from the solution, (c) depositing a solid, and (d) subsequently analyzing the solid. Additionally, the method may comprise the steps of (e) removing the film from the apparatus after the solid has deposited, (f) attaching the film to a spacer plate, wherein the spacer plate has approximately the same array of openings that the masking block has, and optionally sealing the spacer plate with a cover, and (g) analyzing the solid sample to determine the solid form obtained.

According to another exemplary embodiment according to the present teachings, the apparatus of the present invention may utilize a film to form a liquid tight seal between the masking block and the sheet, for example. When a film is used, as the masking block, film, and sheet are pressed together, the film may deform slightly so as to allow a liquid tight seal to form between the film and the masking block.

Figure 1A:
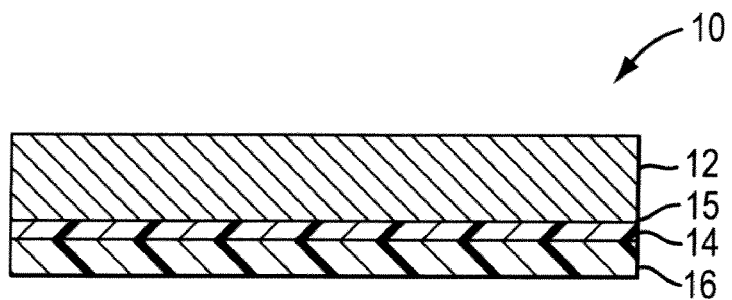
FIGS. 1a and 1b are cross-sectional views of exemplary sample holders according to various aspects of the present teachings.

One exemplary embodiment of the present teachings is illustrated in FIG. 1a, where apparatus 10 may comprise a masking block 12 where the masking block 12 may have a plurality of openings (not shown), a film 14 and a sheet 16, where the film 14 is located between the masking block 12 and the sheet 16. The masking block 12, film 14, and sheet 16 may be placed together such that a liquid tight seal 15 is formed between the masking block 12 and the film 14. Another exemplary embodiment is illustrated in FIG. 1b, where apparatus 10 may comprise a masking block 12 where the masking block 12 may have a plurality of openings (not shown), a film 14, a sheet 16, and a bottom support plate 18.

Figure 1B:
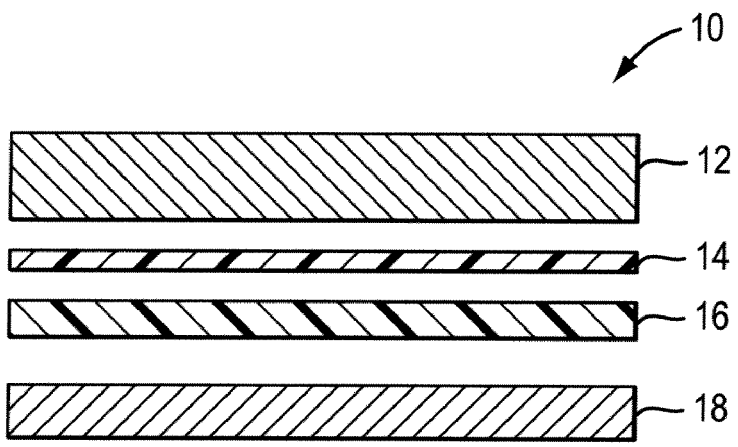

In FIG. 1b, the masking block 12, a film 14, a sheet 16, and a bottom support plate 18 are shown with a gap between, but one of skill in the art will appreciate that this is for illustration purposes only.

In another exemplary embodiment of the present teachings, apparatus 10 may comprise the masking block 12 where the masking block 12 may have a plurality of openings and a sheet 16. The sheet 16 may be of any thickness. The masking block 12 and sheet 16 may be placed together such that a liquid tight seal is formed between the masking block 12 and the sheet 16. This embodiment of the apparatus eliminates the need for a separate film for holding the sample, and may be particularly suited for use with analysis techniques where the energy being analyzed is reflected off of the sample. Non-limiting examples of such analysis techniques may include, for example, reflective x-ray diffraction powder diffraction and Raman spectroscopy including Raman microscopy.

Figure 2A:
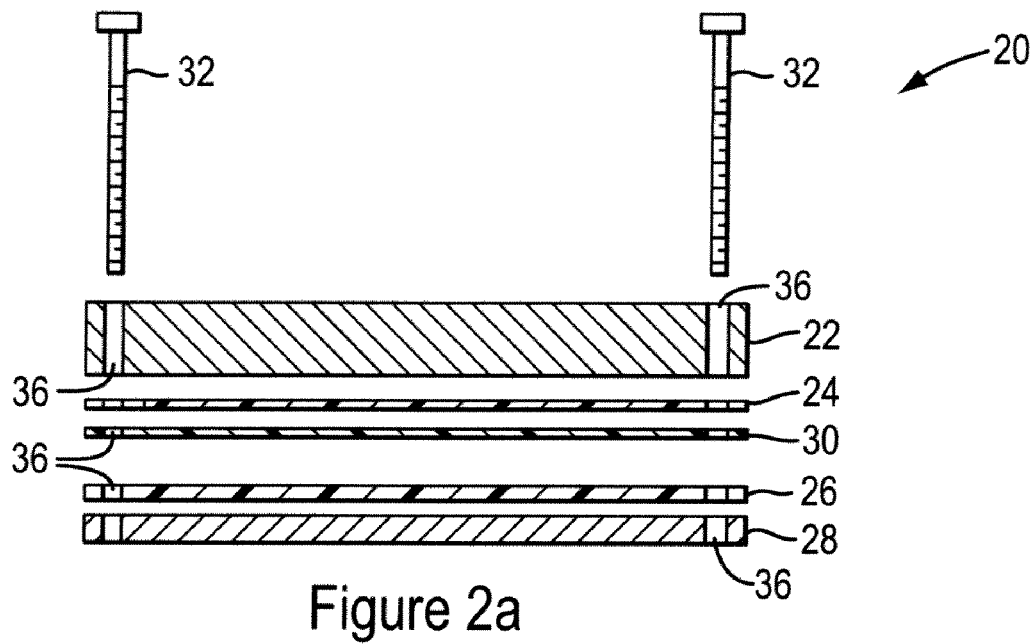
FIG. 2a is a cross-sectional view of an exemplary sample holder according to various aspects of the present teachings.
Figure 2B:
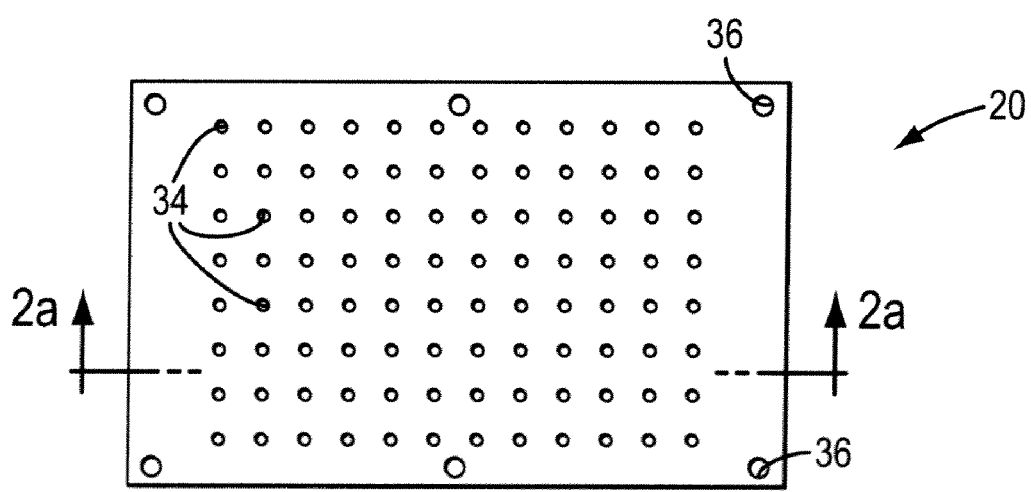

In FIGS. 2a and 2b, masking block 22 may comprise an array of openings 34 for placing a sample solution where the openings go through the masking block 22. The openings may be arranged in any desirable array and have any desired shape (e.g., round, square, oval) and be any desired size. It will be appreciated by those having skill in the art that the size of the hole may be chosen to accommodate the aliquot of a solution to be placed in the hole. The size and shape of the opening may also be chosen according to the desired size and shape of the solid sample to be deposited on the film after the solvent is removed. In the exemplary embodiment of FIGS. 2a and 2b, the well positions of masking block 22 have a configuration substantially similar to that of a microplate with 96 holes that conforms to the American National Standards Institute (ANSI) standard going through masking block 22. Other exemplary embodiments provide for wellplates of other configurations and standards, including but not limited to those set by the ANSI. The use of masking block 22 having the same dimensions as a standard microplate may, for example, be advantageous for using robotics and automated analysis which may already be configured for standard microplates. Therefore, dispensing of the sample and analysis of the resulting solid may be automated.

In exemplary embodiments, the masking block may be comprised of any material that does not chemically alter the solution of interest and may be, but is not limited to, metal, glass, coated materials, plastic, or polypropylene. It will be appreciated that a masking block made from glass or a plastic (e.g., polypropylene) may be used as a disposable masking block, increasing convenience and limiting cross-contamination of samples between trials that may be caused by inadequate washing of a non-disposable masking block.

In exemplary embodiments, the film may be any material that is removable from the masking block after a liquid tight seal has been formed. The film may be chosen to have low or consistent background signal compatible with the desired analytical method for analyzing solid samples deposited in an apparatus, to improve the quality of the analytical data obtained. For example, the film may be chosen to optionally have low crystallinity. The film may also be selected so that it is visually transparent for optical microscopy or birefringement measurements. It may also optionally be selected such that it has a small x-ray diffraction background. In other exemplary embodiments, the film may be chosen from any other suitable material or materials which allow the quality of the analytical data obtained to be improved, such as, for example, the polyimide film sold under the trade name Kapton® by DuPont, the polyester film sold under the trade name Mylar® by DuPont, or polypropylene. In yet further exemplary embodiments, the film may be chosen from a mixture of materials which together allow the quality of the analytical data obtained to be improved, such as, for example, two or more polymer membranes bonded together.

In further exemplary embodiments, the film can have, for example, a thickness ranging from about 1 micron to about 1 millimeter, such as from about 3 microns to about 100 microns, for example, the thickness may be about 25 microns. It will be appreciated that the thinner the film, the less interference the film will have with the desired analytical technique when analyzing solids deposited in the apparatus. However, the film may be thick enough so that it is easily handled without wrinkling or tearing. The film may be used alone or it may be inserted into a frame for ease of handling and stability.

The sheet may be a sheet having the same width and length as the film and/or the masking block, or it may have different dimensions. It may have dimensions chosen to aid in forming a liquid tight seal between the masking block and film. The thickness of the sheet may not be critical, as long a liquid tight seal may be formed. The sheet may be chosen from any material which is suitable for carrying out an embodiment of the invention, such as a polymer, for example, such as, for example, synthetic or natural elastomers.

With reference to FIG. 1a, in an exemplary embodiment of the present teachings a liquid tight seal 15 may be formed between the film 14 and the masking block 12. Alternatively, a liquid tight seal 15 may be formed between the sheet 16 and the masking block 12. The liquid tight seal 15 may be formed by pressing together the masking block 12, film, 14 and sheet 16. The liquid tight seal 15 may be a pressure seal when it is formed this way, or may be any other seal known to those having skill in the art. The masking block 12, film, 14 and sheet 16 may be sealed together by any means known, including, for example, clamping down along the edges and bolting or screwing the pieces together. In some exemplary embodiments, clamping may not be necessary if the masking block is of sufficient weight to maintain a liquid-tight seal.

With reference again to FIG. 1b, in an exemplary embodiment of the present teachings apparatus 10 may further comprise a bottom support plate 18 where the bottom support plate 18 may be placed beneath the sheet 16 on the opposite side from the masking block 12. The bottom support plate 18 may be made of a more rigid material such as, but not limited to metals, plastic, or glass, for example, and may be of any thickness. The bottom support plate 18 may provide support for the film 14 and sheet 16 so that pressure may be placed on the film 14 and the sheet 16 when forming the liquid tight seal between the film 14 and masking block 12 in an exemplary embodiment having a film, or between the sheet 16 and masking block 12 when no film is present. The masking block 12, film 14, and sheet 16 may be pressed together by any means known, including, for example, clamping down along the edges or bolting or screwing the pieces together. It will be appreciated by those having skill in the art that the bottom support plate 18 may be of sufficient thickness to not bend, therefore providing pressure on the sheet 16.

An exemplary apparatus according to the present teachings is shown in FIGS. 2a and 2b. Apparatus 20 may comprise a masking block 22 having an array of openings 34 (as seen in FIG. 2b), a film 24, a sheet 26 and a bottom support plate 28, as described above for apparatus 10. Apparatus 20 may also comprise a non-stick film 30 placed between film 24 and the sheet 26. Alternatively or in addition, the sheet 26 may comprise a non-stick layer. By "non-stick" what is meant is that a film does not adhere to the sheet or to another film. Apparatus 20 may further comprise a set of screw holes 36 which are found at least in masking block 22 and bottom support plate 28. Screws 32 may be threaded through screw holes 36 to exert pressure on the apparatus 20, forming a liquid tight seal between the film 24 and masking block 22. Alternatively, screws 32 may be threaded through nuts attached to the top and/or bottom of the apparatus 20 or through unattached nuts on both the bottom and top of the apparatus 20. With reference to FIG. 2a, as with FIG. 1b, one of skill in the art will appreciate that the gap shown between the masking block 22, film 24, non-stick film 30, sheet 26, and bottom support plate 28 is for illustration purposes.

In another exemplary embodiment, an exemplary apparatus according to the present teachings may be part of a system, wherein the apparatus may be a formation unit wherein the formation unit may comprise a masking block with an array of openings, a sheet, and a film on which an array of solids can be deposited. The film may optionally be located between the masking block and the sheet and may optionally be separable from the masking block and sheet, for example. Additionally, the film may form a liquid tight seal with the masking block. The system may also comprise an analysis unit, where the analysis unit may optionally comprise (a) the film with the array of solids, where the film may optionally be separated from the masking block and the sheet, and (b) a spacer plate, where the spacer plate may have approximately the same array of openings as the masking block. The film may optionally be attached to the spacer plate after being removed from the masking block and the sheet.

In another exemplary embodiment, the formation unit may comprise a masking block where the masking block may have a plurality of openings and a sheet, where an array of solids is deposited on the sheet. The sheet may be of any thickness which can be accommodated by the analytical instrument used to analyze the sample and may optionally be separable from the masking block. The masking block and sheet may be placed together such that a liquid tight seal is formed between the masking block and the sheet. The system may also comprise an analysis unit, where the analysis unit may comprise the sheet with the array of solids, where the sheet may be separated from the masking block, and a spacer plate, where the spacer plate may have approximately the same array of openings as the masking block. The sheet may be attached to the spacer plate after being removed from the masking block.

The film or the sheet with the array of solid material may be attached to the spacer plate so that the solid samples are located within the array of openings in the spacer plate that correspond to the array of openings in the masking block (FIG. 4c). The film or sheet may be attached to the spacer plate by any method or means that allows for a tight seal between the spacer plate and the film or sheet so that no solid material from one opening contaminates a solid material in another opening. Non-limiting examples of methods for attaching the film or sheet to the spacer plate may include, for example, applying spray adhesive to the side of the spacer plate to be contacted to the film or sheet, using double sided tape mastered for the openings of the spacer plate where one side of the tape is applied to the spacer plate and the other to the film or sheet, or the film or sheet may be sealed to the spacer plate by laser, or any attaching means or combination of attaching means known to those of skill in the art.

The spacer plate may be made of any material compatible with the desired analytical technique to be used to analyze the solid material, as well as compatible with the solid sample. In one exemplary embodiment the spacer plate is made from a plastic material that may be disposable. The spacer plate may have a depth similar to the desired thickness of the solid on the film or sheet. The amount of solid required for analysis may be enough to be illuminated to give a strong signal but not too thick to absorb the analyzing radiation. In an exemplary embodiment, the spacer plate is of uniform thickness of approximately 1 mm. In another exemplary embodiment, the spacer plate has a thickness ranging from about 1 mm to about 2 mm.

Figure 3:
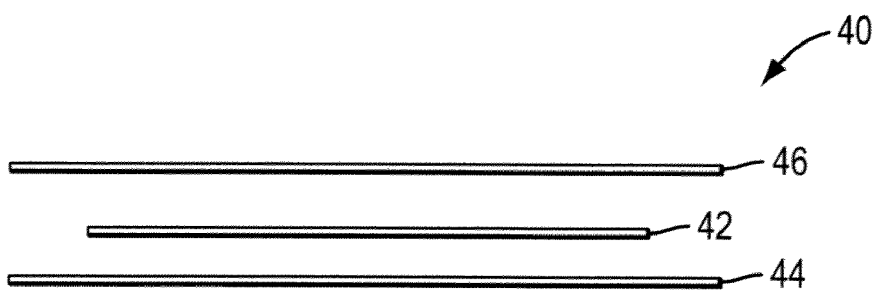
FIG. 3 is a cross-sectional view of an exemplary analysis unit, according to various aspects of the present teachings.

The analysis unit may further comprise a cover, where the cover may be placed on the opposite side of the spacer plate from the film or sheet. The cover may protect the solid material in the openings of the spacer plate from being contaminated or being lost through static or other means of displacing the solid material. A non-limiting example of a cover may be a second film, such as a film chosen from polypropylene, mylar, kapton, or Prolene. It should be noted that a cover may not be desirable if the solid material is to be analyzed by Raman spectroscopy including Raman microscopy. One exemplary embodiment of the analysis unit is shown in FIG. 3. Analysis unit 40 comprises film 44, spacer plate 42 and optional cover, 46. With reference to FIG. 3, as with FIGS. 1b and 2a, one of skill in the art will appreciate that the gap shown between the film 44, spacer plate 42, and optional cover 46 is for illustration purposes.

In another embodiment, the analysis unit 40 may be placed in or attached to a holder 49 (FIGS. 4a-4b). If analysis of the solid samples in the analysis unit is performed on an automated system, a holder 49 for the analysis unit may be required.

The present invention also provides methods of forming a solid and analyzing the solid to determine the solid form. The method may comprise the step of placing at least one aliquot of a liquid containing at least one organic or inorganic chemical compound in a well of the formation unit where the formation unit may comprise a masking block comprising an array of openings, a film and a sheet, where the film is between the masking block and the sheet. It will be appreciated that the organic or inorganic chemical compound may dissolve in the liquid to form solution. The organic or inorganic chemical compound may also form, for example, a slurry, semisolid, paste, or wet solid with the liquid. Examples of liquids suitable for the invention include solvents such as methanol, dichloroethane, ethanol, water, acetone, THF, DMF and other organic solvents or mixtures thereof known to those of skill in the art. Examples of organic or inorganic compounds include active pharmaceutical ingredients. When a solution is formed, it may be formed ex situ or in situ, where the solution may be added to the opening or a solid sample and a solvent may be added separately to the opening and the sample solution formed in situ. When a slurry, semisolid, paste, or wet solid is formed, it may be formed ex situ or in situ, where the slurry or paste may be added to the opening or a solid sample and a solvent may be added separately to the opening and the sample slurry or paste formed in situ. The film may form a liquid tight seal with the masking block so that any material placed in the openings of the masking block may not leak from into another opening. Different sample solutions, slurries, semisolids, pastes, or wet solids may be placed in each opening of the masking block or the same sample solution, slurry, or paste, but different aliquots, may be placed in each opening of the masking block. Alternatively, the same sample solution, slurry, semisolid, paste, or wet solid in the same aliquot may be placed in some or all of the openings.

The method may also comprise the steps of removing liquid from the sample to form the solid material, and then analyzing the solid material to determine the solid form. Methods for removing liquids from the sample under study include, for example, evaporation, wicking, aspirating, and any other methods known to those of skill in the art including combinations of methods. Once the liquid is removed, then the sample remaining can be deemed a "solid." The solid may be in the form of a crystalline solid or x-ray amorphous solid. It may be wet with solvent. It may also be in the form of a slurry, semisolid, or paste, for example.

The solid may be analyzed and characterized by any suitable analytical method including, but not limited to, x-ray powder diffraction in transmission mode or reflection mode, light microscopy or Raman spectroscopy including Raman microscopy. In some embodiments, the resulting analysis may reveal that the solid form is crystalline or contains crystals. The analysis may also reveal that the sample is x-ray amorphous by which is meant that there are no peaks in the diffraction pattern, which appears as one or more halos. Such patterns represent samples that may be, for example, nanocrystalline, glasses, or a combination of the two. The resulting analysis may also reveal that the solid form of the solid is a multicomponent crystal such as a solvate or hydrate. Such multicomponent crystals are generally referred to as cocrystals. In a pharmaceutical cocrystal, the active pharmaceutical ingredient is generally referred to as "the host," whereas all other molecules which help make up the unit cell are generally referred to as "guests." Other examples of cocrystals include those where the active pharmaceutical ingredient is a salt and the guest is a carboxylic acid.

The method may further comprise the steps of removing the film from the formation unit and attaching it to a spacer plate, forming an analysis unit. The spacer plate may have an array of openings similar to the masking block. After the film with the solid material is attached the spacer plate, the solid material is analyzed to determine the solid form.

It should be understood, of course, that the foregoing relates to exemplary embodiments of the invention and that modifications may be made without departing from the spirit and scope of the invention as set forth in the following claims.

Although the present invention herein has been described with reference to various exemplary embodiments, it is to be understood that these embodiments are merely illustrative of the principles and applications of the present invention. Those having skill in the art would recognize that a variety of modifications to the exemplary embodiments may be made, without departing from the scope of the invention.

Moreover, it should be understood that various features and/or characteristics of differing embodiments herein may be combined with one another. It is therefore to be understood that numerous modifications may be made to the illustrative embodiments and that other arrangements may be devised without departing from the scope of the invention.

Furthermore, other embodiments of the invention will be apparent to those skilled in the art from consideration of the specification and practice of the invention disclosed herein. It is intended that the specification and embodiments herein be considered as exemplary only, with a scope and spirit being indicated by the following claims.

What is claimed is:

1. An apparatus for the formation of solids and analysis of solid forms comprising:
    a masking block with an array of openings;
    a sheet;
    a film, wherein the film is located between the masking block and the sheet and wherein the film forms a liquid tight seal with the masking block; and
    a bottom support plate, wherein the sheet is located between the film and the bottom support plate.

2. The apparatus of claim 1, further comprising a non-stick film, wherein the non-stick film is located between the film and the sheet.

3. The apparatus of claim 1, wherein the liquid tight seal is a pressure seal.

4. The apparatus of claim 1, wherein the film comprises polypropylene, mylar, kapton or Prolene.

5. The apparatus of claim 1, wherein the film is visually clear.

6. A system for the formation of solids and analysis of solid forms comprising:
   a formation unit, wherein the formation unit comprises:
      a masking block with an array of openings,
      a sheet, and
      a film on which an array of solids is deposited,
         wherein the film is located between the masking block and the sheet and separable from the masking block and sheet, and
         wherein the film forms a liquid tight seal with the masking block; and
   an analysis unit, wherein the analysis unit comprises:
      the film with the array of solids, wherein the film is separated from the masking block and the sheet,
      a spacer plate, wherein the spacer plate has approximately the same array of holes as the masking block, and
      wherein the film is attached to the spacer plate.

7. The system of claim 6, wherein the film is attached to the spacer plate by adhesive.

8. The system of claim 6, wherein the analysis unit further comprises a cover, and wherein the cover is on an opposite side of the spacer plate than the film.

9. The system of claim 6, wherein the formation unit further comprises a bottom support plate, and wherein the sheet is located between the film and the bottom support plate.

10. The system of claim 6, wherein the formation unit further comprises a non-stick film, and wherein the non-stick film is located between the film and the sheet.

11. The system of claim 6, wherein the liquid tight seal is a pressure seal.

12. A method of forming a solid and analyzing the solid form of the solid comprising the steps of:
   placing at least one aliquot of a liquid containing one or more solvents and at least one organic or inorganic chemical compound in an opening of a formation unit to form a sample, wherein the formation unit comprises a masking block comprising an array of openings, a film, and a sheet, wherein the film is located between the masking block and the sheet, and wherein the film forms a liquid tight seal with the masking block;
   removing liquid from the sample to deposit a solid;
   removing the film from the masking block and the sheet;
   attaching the film to a spacer plate, wherein the spacer plate has approximately the same array of holes as the masking block, and wherein the film is attached to the spacer plate before analyzing the solid to determine the solid form; and
   analyzing the solid to determine the solid form of the solid.

13. The method of claim 12, wherein the solid form is crystalline.

14. The method of claim 12, wherein the solid form is x-ray amorphous.

15. The method of claim 12, wherein the sample is a solution.

16. The method of claim 12, wherein the solid form is a cocrystal.

17. The method of claim 12, wherein the film is separated from the masking block and the sheet before analysis.

18. The method of claim 12, wherein the solid form is analyzed by x-ray powder diffraction in transmission mode, x-ray powder diffraction in reflection mode, light microscopy, Raman spectroscopy, Raman microscopy, infrared spectroscopy, near-infrared spectroscopy, or a combination thereof.

19. The method of claim 12, further comprising the step of placing a cover on the spacer plate, the cover being on the opposite side of the spacer plate from the film.

20. A system for the formation of solids and analysis of solid forms comprising:
   a formation unit, wherein the formation unit comprises:
      a masking block with an array of openings, and
      a sheet on which an array of solids is deposited,
         wherein the sheet is separable from the masking block, and wherein the sheet forms a liquid tight seal with the masking block; and
   an analysis unit, wherein the analysis unit comprises:
      the sheet with the array of solids, wherein the sheet is separated from the masking block,
      a spacer plate, wherein the spacer plate has approximately the same array of holes as the masking block, and wherein the sheet is attached to the spacer plate.

21. The system of claim 20, wherein the sheet is attached to the spacer plate by adhesive.

22. The system of claim 20, wherein the analysis unit further comprises a cover, and wherein the cover is on an opposite side of the spacer plate than the sheet.

23. The system of claim 20, wherein the formation unit further comprises a bottom support plate, and wherein the sheet is located between the masking block and the bottom support plate.

24. A method of forming a solid and analyzing the solid to determine the solid form comprising the steps of:
   placing at least one aliquot of a liquid containing one or more solvents and at least one organic or inorganic chemical compound in an opening of a formation unit to form a sample, wherein the formation unit comprises a masking block comprising an array of openings and a sheet, wherein the sheet forms a liquid tight seal with the masking block;
   removing liquid from the sample to deposit a solid;
   removing the sheet from the masking block;
   attaching the sheet to a spacer plate, wherein the spacer plate has approximately the same array of holes as the masking block; and
   analyzing the solid to determine the solid form.

25. The method of claim 24, further comprising the step of placing a cover on the spacer plate, the cover being on the opposite side of the spacer plate from the sheet.

* * * * *